(12) United States Patent
Vogel et al.

(10) Patent No.: US 9,795,511 B2
(45) Date of Patent: Oct. 24, 2017

(54) DEVICE FOR LASER CUTTING WITHIN TRANSPARENT MATERIALS

(71) Applicant: UNIVERSITÄT ZU LÜBECK, Lübeck (DE)

(72) Inventors: Alfred Vogel, Luebeck (DE); Norbert Linz, Luebeck (DE); Sebastian Freidank, Luebeck (DE)

(73) Assignee: Universitaet zu Luebeck, Luebeck (DE)

( * ) Notice: Subject to any disclaimer, the term of this patent is extended or adjusted under 35 U.S.C. 154(b) by 24 days.

(21) Appl. No.: 14/355,280

(22) PCT Filed: Sep. 2, 2013

(86) PCT No.: PCT/DE2013/100312
§ 371 (c)(1),
(2) Date: Apr. 30, 2014

(87) PCT Pub. No.: WO2014/036995
PCT Pub. Date: Mar. 13, 2014

(65) Prior Publication Data
US 2015/0164689 A1    Jun. 18, 2015

(30) Foreign Application Priority Data

Sep. 5, 2012  (EP) .................................... 12183091

(51) Int. Cl.
*A61F 9/008*  (2006.01)
*B23K 26/38*  (2014.01)
(Continued)

(52) U.S. Cl.
CPC ........ *A61F 9/0084* (2013.01); *A61F 9/00827* (2013.01); *A61F 9/00836* (2013.01);
(Continued)

(58) Field of Classification Search
CPC ............ A61F 9/008; A61F 2009/00872; A61F 9/0084; A61F 9/00827; A61F 9/00836;
(Continued)

(56) References Cited

U.S. PATENT DOCUMENTS 5,507,799 A * 4/1996 Sumiya ............... A61F 9/00804
219/121.6
5,523,543 A * 6/1996 Hunter, Jr. ............ G01J 1/4257
219/121.62
(Continued)

FOREIGN PATENT DOCUMENTS

DE    102007028042 B3    8/2008
EP         1787607 A1    5/2007

OTHER PUBLICATIONS

"Computational Nonlinear & Quantum Optics Group" http://cnqo.phys.strath.ac.uk/research/quantum-theory-of-light/optical-angular-momentum/producing-light-with-oam/.*

*Primary Examiner* — Lynsey Eiseman
*Assistant Examiner* — Amanda Steinberg
(74) *Attorney, Agent, or Firm* — Patent Central LLC; Stephan A. Pendorf

(57) ABSTRACT

A laser cutting device for transparent material (23), which device is designed to focus the laser light (2) into a plurality of predetermined spots within the material (23), wherein the spots lie on a predetermined cutting line or cutting area (24) running substantially perpendicularly to the direction of incidence of the laser light (2), wherein the device comprises means for mode conversion (3) into laser light having a helical phase front (5), which means can be brought into and out of the beam path of the laser light (2).

10 Claims, 4 Drawing Sheets

Figure 3:
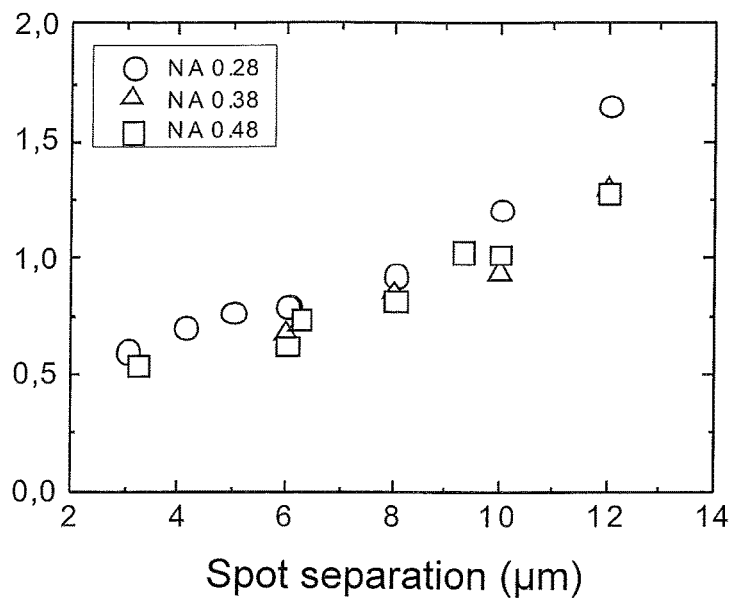
Figure 3:
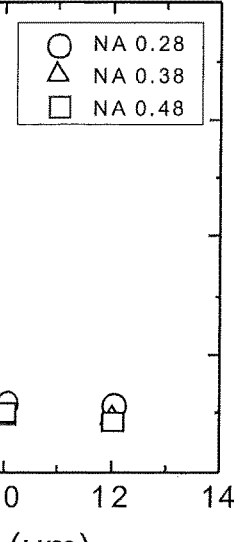

(51) Int. Cl.
*B23K 26/064* (2014.01)
*B23K 103/00* (2006.01)

(52) U.S. Cl.
CPC ............ *B23K 26/064* (2015.10); *B23K 26/38* (2013.01); *A61F 2009/0087* (2013.01); *A61F 2009/00853* (2013.01); *A61F 2009/00872* (2013.01); *A61F 2009/00887* (2013.01); *A61F 2009/00897* (2013.01); *B23K 2203/32* (2015.10); *B23K 2203/50* (2015.10)

(58) Field of Classification Search
CPC ........ A61F 9/00814; A61F 2009/00853; A61F 2009/0087; A61F 2009/008487; A61F 2009/00848; A61F 2009/0088; A61F 2009/00897; A61F 2009/00887; B23K 26/38; B23K 26/402; B23K 26/064; A23K 2203/32
USPC .......................................... 606/4, 5
See application file for complete search history.

(56) References Cited

U.S. PATENT DOCUMENTS

| | | | | |
|---|---|---|---|---|
| 5,928,221 | A | * | 7/1999 | Sasnett .................. A61F 9/008 606/10 |
| 6,373,876 | B1 | * | 4/2002 | Dulaney ............ B23K 26/0069 219/121.68 |
| 2004/0215175 | A1 | * | 10/2004 | Feklistov ................ A61F 9/008 606/4 |
| 2004/0233388 | A1 | * | 11/2004 | Artsyukhovich ... A61F 9/00821 351/216 |
| 2005/0107773 | A1 | * | 5/2005 | Bergt .................... B23K 26/08 606/4 |
| 2005/0245915 | A1 | | 11/2005 | Loesel et al. |
| 2006/0087550 | A1 | * | 4/2006 | Kang ................ B23K 26/0648 347/224 |
| 2008/0243108 | A1 | | 10/2008 | Murakami et al. |
| 2009/0318906 | A1 | | 12/2009 | Koenig et al. |
| 2010/0134869 | A1 | * | 6/2010 | Bernet .................. G02B 5/001 359/290 |
| 2010/0163540 | A1 | | 7/2010 | Vogel et al. |
| 2012/0038842 | A1 | * | 2/2012 | Wilkinson ............ G02F 1/1393 349/33 |

\* cited by examiner

Fig. 1 a) (prior art)
Linear 
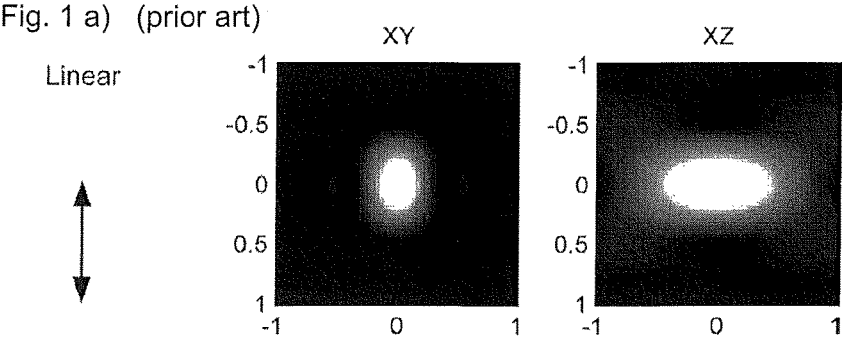
Fig. 1 b) (prior art)
Azimuthal 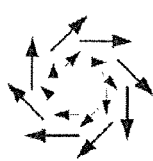
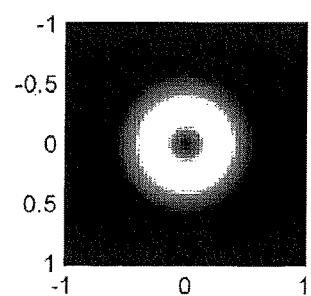 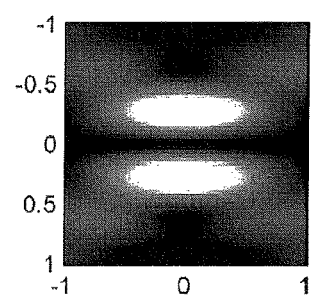
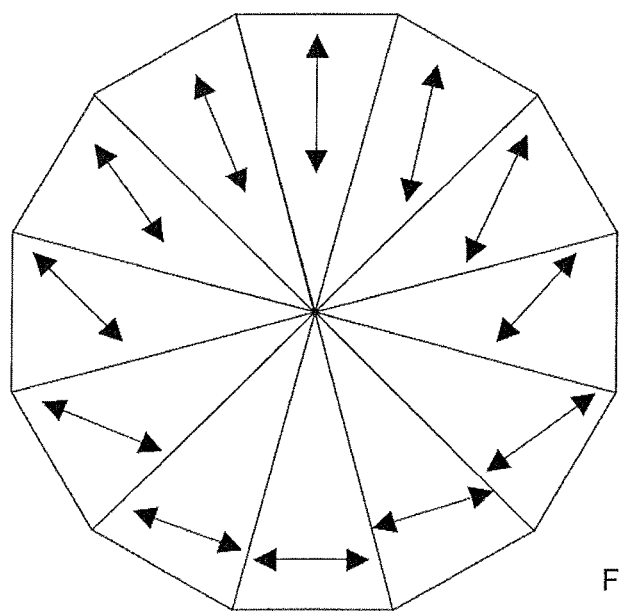
Fig. 2 (prior art)

Fig. 5 a)
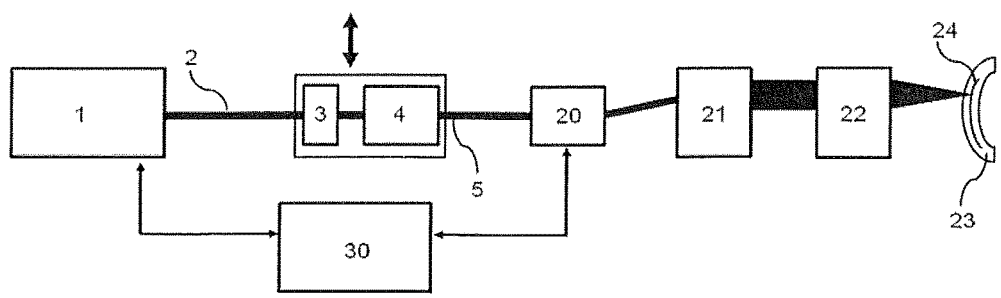
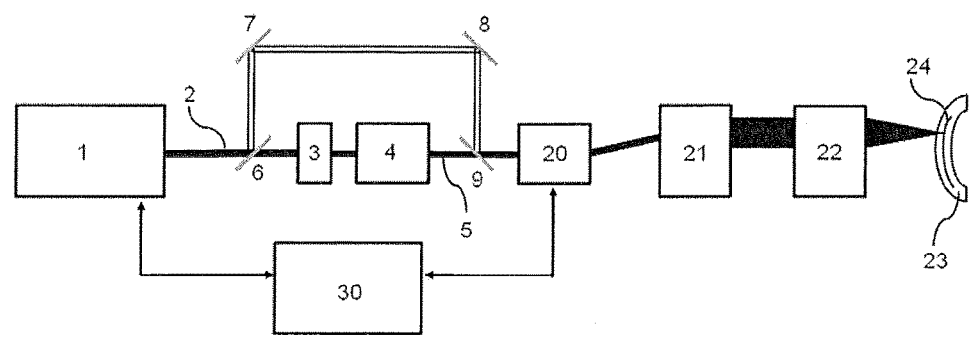
Fig. 5 b)

DEVICE FOR LASER CUTTING WITHIN TRANSPARENT MATERIALS

BACKGROUND OF THE INVENTION

Field of the Invention

The invention relates to a laser cutting device for a transparent material which is adapted to focus the laser light (laser radiation) into a plurality of predetermined spots in the material, wherein the spots are located on a predetermined cutting line or cutting area, which is substantially perpendicular to the direction of irradiation of the laser light. The invention also relates to a device for laser processing of biological tissue, particularly of the living eye.

Description of the Related Art

The production of fine effects in laser material processing requires the localized deposition of low quantities of energy. In materials transparent to laser light, such as glass, quartz water, non-pigmented body tissues or cells, a localized energy deposition can be carried out by multi-photon processes in the form of multiphoton ionization and avalanche ionization, which lead to the formation of plasma (quasi-free charge carriers in the material comprising a mixture of electrons and ions). Since the occurrence of multi-photon processes are not linearly dependent on the laser light intensity, one speaks of "nonlinear absorption". And since the plasma formation rate above a threshold, which depends on material and laser parameters, increases extremely strongly, the plasma formation process in this parameter range is also referred to as "optical breakdown".

High precision material processing by nonlinear absorption requires that spatially localized reproducible small amounts of energy must be introduced (deposited) in the material. The good spatial localization is achieved primarily by focusing the laser pulses by means of aberration-free optics of high numerical aperture.

When dissecting within transparent materials, often a cut or incision is desired, which does not occur along the direction of incidence of the laser light, but at a predetermined angle to the direction of incidence. Frequently, the dissection is carried out even perpendicular or approximately perpendicular to the direction of irradiation in order to produce a cut which is aligned parallel or nearly parallel to the surface of the transparent medium. Often not only is a cut line produced, but the cuts are made in two dimensions along a cutting surface or area which is essentially parallel to the surface of the material, in order to separate a layer of the material. This occurs, for example, in corneal refractive surgery (laser in-situ keratomileusis, in short: LASIK).

For the actual incision, focused laser pulses are applied next to each other in a grid of points. At each grid point (in the following also: spot), plasma is generated, which disintegrates the transparent material in the focal volume, and at a sufficiently high energy density results in a micro-explosion, which creates a hollow space (or a transient cavitation bubble in the case of liquids or biological tissue).

The respective effective cutting mechanism depends on the distance between the grid points and the power density of the plasmas. The energy density is determined by the laser pulse energy and the material-dependent threshold for optical breakdown, which in turn is dependent on the laser pulse length and the laser wavelength and the laser light quality and the convergence angle (numerical aperture) of the focused laser light. All other irradiation parameters being equal, the plasma energy density is adjustable over a wide range by varying the laser pulse energy.

The cutting mechanisms can be divided into two categories and are commonly referred to as disintegration mode and splitting mode.

Disintegration Mode:

If laser plasmas are generated with less energy and electron density, then the free electrons cause disintegration by bond breaks of the material in the laser foci. This is associated with evaporation of material or material decomposition. The decomposition of material in biological tissues leads, for example, to the formation of gas bubbles with lifetimes in the range of milliseconds to seconds, which, while not contributing to the cutting effect, can serve as an indicator for the material decomposition. In the event of overlap of the focus volume and a sufficiently large density of bond breakage, a contiguous cut can be generated. Although the individual pulse energy is small, the disintegration of a continuous layer of material requires the accumulated effect of a large number of laser pulses and therefore a relatively high total energy.

Splitting Mode:

In the splitting mode, the lateral distance D in the grid of focus points is selected to be greater than the focal diameter D, and is usually about 6-10 microns. Here, a continuous cut can only be produced by the micro-explosion effect of plasmas and the merging of the transient cavities (cavitation bubbles) generated by plasmas. For the generation of the voids, plasmas of higher energy density are required than for the disintegration mode. In a material having a layered structure (for example the corneal stroma of the eye) the merging of hollow spaces into an incision is facilitated. The cutting process is therefore a cleaving process driven by the expansion of the laser-produced cavitation bubbles, which preferably extends along mechanical areas of weaknesses. Analogies for this are the splitting of slate taking advantage of local mechanical action or the splitting of knot-free wood along the grain with an axe. Although the single pulse energy required for the generation of micro-explosions in the splitting mode is greater than in the disintegration mode, the total energy required is generally lower because it is not necessary to change the physical state of a continuous layer of material, but rather a mechanical separation along weaknesses in the material takes place and thus a lower number of individual pulses is necessary. The loss of material is accordingly also lower than in the disintegration mode.

With both cutting mechanisms, the average precision is largely determined by the length of the laser plasma, which in turn depends on the length of the laser focus. Focus diameter d and focal length l are, at full utilization of the aperture of the cutting lens, given by:

$$d = 1{,}22 \frac{\lambda}{NA} \tag{1}$$

$$l = 4\frac{d^2}{\lambda} \approx 6\frac{\lambda}{NA^2} \tag{2}$$

Here $\lambda$ represents the wavelength of the of the laser light used and NA is the numerical aperture of the cutting lens edge, which is associated with the half-opening angle $\alpha$ by $NA = n \sin_\alpha$ (n being the refractive index of the medium in which the light is focused). At the threshold for plasma formation, the plasma length is similar in size to the focal length l and increases with increasing laser pulse energy. The cutting precision is defined by the localizability of the cut in the irradiation direction and the cutting width, both of which are associated with the plasma length. From equation (2) it can be seen that the cutting accuracy is increased if the numerical aperture is increased or the wavelength $\lambda$ is reduced.

The currently commercially available femtosecond laser systems for refractive corneal surgery operate at wavelengths in the near infrared between 1030 nm and 1060 nm. With these systems, attempts at an increase in the cutting precision mainly involve increasing the NA. Alternatively, the use of ultraviolet laser radiation can be considered. The wavelength shortened to about ⅓ compared to infrared femtosecond pulses leads according to equation (2) to a considerable improvement of the cutting accuracy.

The document EP 1787607 A1 proposes the use of a pulsed ultraviolet light at wavelengths between about 190 nm and 380 nm for LASIK treatment, wherein the UV-pulses are generated by frequency multiplication from infrared femtosecond pulses and have a pulse duration up to a maximum of 10 ps. The authors of EP 1787607 A1 assume that UV pulses with pulse energies of about 10 nJ and repetition rates between 100 and 500 kHz on the one hand lead to precise cuts in the corneal tissue and on the other hand are almost completely absorbed in the cornea or lens. Energy inputs due to residual transmissions into the retina are considered virtually impossible. However, it is noteworthy that no mention is made of the unwanted side-effect of photochemical changes of the tissue in the area of UV radiation.

The publication DE 10 2007 028 042 B3 shows that a very fine laser processing of transparent materials with time-smooth ultraviolet nanosecond pulses is possible. In particular, laser pulses with 355 nm wavelength and 0.7 ns pulse duration can be used to generate LASIK flaps in the cornea, wherein the cutting is in the splitting mode (Vogel A, Linz N, Freidank S, Faust S, Schwed S (2011b) LASIK Flaperzeugung mit UV Subnanosekundenpulsen, The Ophthalmoscope 12, 2011. 32-35). The advantage of this approach is the possibility of direct generation of the ultraviolet laser light with a fiber reinforced microchip laser, in which a significant potential for reducing costs can be seen. In addition, when using nanosecond pulses, due to the lower peak power nonlinear propagation effects and filamentation can better be avoided than with femtosecond pulses.

U.S. 2005/245915 A1 discloses a method for making a cut along a dome-shaped sectional area of living eye corneal stroma tissue with an infrared femtosecond pulse laser. The sectional area is substantially parallel to the corneal surface and also substantially perpendicular to the direction of irradiation of the laser light. A grid of focus positions is predetermined on the sectional area, wherein in each of the spots a bubble of a predetermined diameter is to be produced. The laser focus diameter is thus less than or equal to the bubble diameter. The spots should—perpendicular to the beam direction—have distances to the nearest neighbor, which correspond approximately to the bubble diameter. As far as can be determined, the laser cutting is carried out in the splitting mode described above, and not in the disintegration mode.

The combination of a spot grid in accordance with, for example, U.S. 2005/245915 A1 with an ultraviolet laser processing according to DE 10 2007 028 042 B3 to obtain a more precise, in particular, along the beam direction sharply localized planar cuts turns out to indeed be successful especially for processing biological tissues. However, the significant reduction in spot size of the UV laser required, with a constant individual pulse energy, a higher grid spot density, and thus the total energy to be deposited for a planar cut is significantly higher than with the use of an infrared femtosecond pulse laser. Especially for living tissue is produced a dose problem, because the extent of possible UV-induced photochemical side effects is scaled according to the reciprocity law of Bunsen and Roscoe with the total irradiation dose ($J/cm^2$).

High cutting speed and precision and at the same time minimal photomechanical side effects are generally competing objectives, and with the use of a UV laser, there must also be taken into consideration the minimization of photochemical side effects. A high cutting speed requires not only a high laser pulse repetition rate but also a large grid point spacing. If latter is larger, this brings advantageously the reduction of the total cutting energy and thereby minimizes photochemical effects. If the grid point spacing, however, is made too large, the single pulse energy must be increased so much that the cutting precision suffers and the extent of possible side effects caused by the mechanical effect of laser-produced shock waves and cavitation bubbles increases significantly. The same adverse effect occurs when with constant grid spacing the focus diameter is greatly reduced: now the single pulse energy must be increased, to enlarge the splitting distance to the necessary extent.

Against this background, one can search for ways to improve, directed at the shaping of the laser focus and the produced plasma.

The prior art already knows methods for focus formation for laser material processing in transparent media. They are aimed generally at a focus elongation, if possible, even with a reduction of the lateral diameter: for example, a Bessel beam is used instead of a Gaussian beam, to produce in comparison to the Gaussian beam a greatly extended focus area (McGloin D, Dholakia K (2005) Bessel beams: Diffraction in a new light. Contemp. Phys. 46:15-28). Bessel beams are suited for the optimization of cutting section in the direction of incidence of the laser, such as the edge cut in LASIK flap creation.

Additional ways of increasing the plasma length are obtained by nonlinear beam light propagation direction (self-focusing by the generated plasma) and filamentation in transparent media. These are used for the production of elongated laser effects, bore holes and channels with large aspect ratio (Ashkenazi D, Varel H, Rosenfeld A, Henz S, Herrmann J, Campbell E E B (1998) Application of self-focusing of ps laser pulses for three-dimensional microstructuring of transparent material. Appl. Phys. Lett. 72:1442-1444).

If one uses laser pulses of high power, and the cutting direction runs substantially perpendicular to the laser beam direction, then a focus elongation by nonlinear propagation of the beam and filamentation is usually to be avoided if possible. Disturbance of the incision guidance through focus elongation were described for femtosecond LASIK (Arnold C L, Heisterkamp A. Ertmer W, Lubatschowski H (2004) Streak formation as side effect of optical breakdown during processing the bulk of transparent Kerr media with ultrashort laser pulse. Appl. Phys. V 80:247-253).

So-called vortex beams have a larger cross-section than focusing Gaussian beams at the same focusing angle. Thus, they have an at least 4-fold higher self-focusing threshold than Gaussian beams (Vuong L T et al. (2006) Collapse of optical vortices. Phys. Rev. Lett. 96:133901 (4pp)).

The name "Vortex Beam" stems from the fact that the intensity distribution on the optical axis has a zero and one can understand this singularity as an eddy in the electromagnetic field. Laguerre-Gaussian (LG) modes of propagation of light have this property, wherein the fundamental mode is designated LG (0.1) (Yao and Padgett, "Orbital angular momentum: origins, behavior and applications", Advances in Optics and Photonics 3, 161-204 (2011)).

The LG modes form a complete set of modes, according to which light with helical phase fronts ("helically phased beams") can be developed. The individual helical photons carry thereby angular momenta. Helical laser light may be produced from non-helical laser light (conventionally: Gaussian beam, but not limited thereto), if the non-helical beam is transmitted through a helical phase plate ("spiral phase plate"), a specially designed computer-generated diffraction grating ("diffractive optical element", often also referred to as "subwavelength structure"), an electronically addressable spatial light modulator ("spatial light modulator") or a cylindrical lens array (Yao and Padgett, "Orbital angular momentum: origins, behavior and applications", Advances in Optics and Photonics 3, 161-204 (2011)). However, the aforementioned means for mode conversion of non-helical into helical laser light are either difficult to prepare, suitable only for limited laser power (e.g., phase plates made of plastic and diffraction grating designed as a structured metallization or as a matrix of liquid crystals) or make demands on the non-helical light, which are not met by conventional laser sources for materials processing (e.g. the occurrence of certain higher Gaussian modes).

An efficient mode conversion for high power laser applications can, however, be achieved by helical phase plates of quartz glass or an other light-stable birefringent material (Machavariani G, Lumer Y, Moshe I, Meir A, Jackel S (2007) Efficient extracavity generation of radially and azimuthally polarized laser beams. Opt. Lett. 32: 1468-1470).

An ideal conversion in the Laguerre-Gaussian fundamental mode LG (0,1) would be achieved by an optical device which produces a phase shift which rises during the rotation around the optical axis by 360 degrees continuously from zero to $2\pi$. However, such components with a continuous phase shift can not yet be produced from a material since it would need to withstand the very high laser power.

The ideal situation is therefore approximated by the use of segmented phase plates, wherein the approximation is all the better and the more increased in efficiency, the higher the number of segments. By a downstream spatial frequency filtering the light scattered at the sector boundaries can be eliminated and a focal intensity distribution be create, which is very close to the ideal Laguerre-Gaussian (0, 1) mode (Machavariani et al. 2007).

As further state of the art, there is to be mentioned the work of Junichi Hamazaki et al. "Optical-vortex laser ablation", OPTICS EXPRESS, Vol. 18, No. 3, pp. 2144 et seq, (2010). Hamazaki et al. investigate laser ablation of tantalum plates with single laser pulses, which exhibit in the machining plane a ring-shaped ("annular") light intensity distribution. For this, Gaussian laser light is either converted by a helical phase plate into a vortex beam, or directed through a spatial notch filter (SNF), which leads to a "nonvertex annular beam" (NVAB). Both beam types are used for material removal, and the achieved quality of the machined surface or area is compared for these cases. Vortex beams prove to be beneficial for laser ablation of solids.

The energy input by the laser light takes place in Hamazaki et al., however, by linear absorption at the solid surface and not in a laser focus that is well below the machining plane. The annular intensity distribution of NVAB arises namely only in the Fresnel diffraction image in front of the focal plane, but not in the far-field diffraction pattern. There, an intensity maximum is located in the center of the light spot and the light intensity as a whole is much higher due to the smaller spot diameter. The reason is explained by the authors on page 2146, paragraph 3: "Since NVAB is not an eigen-solution of the paraxial equation, the dark spot in the center disappears in the focal plane".

In that respect, from the therein described advantages of vortex beams in ablating, no conclusion can be drawn on material processing in the laser focus, in particular with regard to cut guidance on the inside of a transparent material.

U.S. 2008/243108 A1 discloses a therapeutic laser system for photocoagulation or iridotomy, that for the purpose of providing a beam profile with uniform ("top-hat") or slightly annular intensity distribution with at the same time selectable spot diameter on the tissue to be treated, provides an additional device with a plurality of diffractive optical elements ("diffraction optical elements", DOE). The DOEs are to be understood as diffraction structures, which, by means of interference, form the previously expanded and collimated laser beam. They can, according to the user's choice, for example, be slewed (swung or slid) into and out of the beam path of the Gaussian laser beam via the electrical control of a stepper motor, if, for example, all the DOEs are arranged in the edge region of a rotating disk. Here too, the energy input occurs by linear absorption, and the working plane is not coincident with the focal plane.

The device described in U.S. 2008/243108 A1 is hardly suitable for laser cutting in the interior of a transparent material, because the beam shaping by DOEs brings with it an along the beam direction variable beam profile (as also in NVAB with Hamazaki et al). One can not be sure that the location of the highest intensity lies in the focal plane, but rather expect areas of comparable high intensity ("hot spots") before and/or behind the focal plane, which runs contrary to the intention of a precise cut at a predetermined depth. A light distribution with no "hot spots" outside the focal plane can only be achieved with a light beam light propagation mode in which the beam profile remains constant along the propagation direction. These include Gaussian or Laguerre-Gaussian modes, but not the light distributions generated by DOE.

As the closest prior art there is a laser cutting device for transparent material according to the teaching of U.S. 2005/245915 A1, which is adapted in particular to focus the laser light inside a transparent material, and produce by multiphoton processes plasmas in the laser focus, where the material processing is to take place.

BRIEF SUMMARY OF THE INVENTION

It is the object of the invention to improve a laser cutting device for a transparent material in such a way that the precise performance of laser cuts in the material along a cut line or cut surface or area which is perpendicular to the direction of irradiation of the laser light is achieved with substantially fewer spots or a lower total dose of energy than required in the prior technology and thus avoid photochemical and photomechanical side effects.

BRIEF SUMMARY OF THE INVENTION

The object is solved by a laser cutting device for a transparent material which is adapted to focus the laser light into a plurality of predetermined spots in the material, wherein the spots are located on a predetermined cutting line or surface, which runs perpendicular to the direction of irradiation of the laser light, characterized in that the device includes a means that can be introduced into and removed from the beam path of the laser light for mode conversion into laser light having a helical phase front.

The dependent claims describe advantageous embodiments.

To the best knowledge of the inventors, it has not yet been proposed to use laser light with helical phase fronts (shortened in the following: helical laser light) for making cuts in transparent material. Certainly, the inventors are not aware of any suggestion of the use of helical laser light in medical therapy, particularly in the laser treatment of the eye.

Helical laser light always has an optical vortex, is thus a typical vortex beam. Its properties recognized as essential to the invention include the fact that the focusing of the laser beam leads to a toroidal helical light intensity distribution and consequently also a toroidal region of plasma generation, which is greater than the focus cross section of a Gaussian beam.

An example of the intensity distribution in the focal region of an azimuthally polarized laser beam (an example of helical laser light) compared with the focal region of a linearly polarized laser beam can be seen in FIG. 1 (from Hao X, Kuang C, Wang T, Liu X (2010) Effects of polarization on the de-excitation dark focal spot in STED microscopy. J. Opt. 12:115707 (8pp)). It can be seen that the focal diameter compared to the value of a linearly polarized beam is increased by a factor of 2-3, whereas the focal length remains substantially unchanged.

The basic idea of the invention is that vortex beams are adapted to produce, relative to a linearly polarized Gaussian beam, an at least doubled focal diameter with approximately the same focal length, and thus allow a larger spot interval, without having to increase the one-pulse energy. This increases the cutting speed and prevents adverse mechanical side effects as well as—in the case of a UV-laser beam for processing living tissue—exceeding a tolerable dose of radiation.

It is known to be possible to manufacture optical elements which, when introduced into the beam path of a conventional linearly polarized Gaussian beam, form a vortex beam (for example with azimuthal polarization). Such optical elements, referred to in the following as means for mode conversion into helical laser light (or short: means for mode conversion) are, according to the invention, to be arranged in the device that they can be introduced into and be removed from the beam path of the laser as needed. In this way, the laser cutter device makes available several forms focus according to the user's choice.

The conventional processing laser beam (e.g., a Gaussian beam) can thus during use—preferably by slewing-in a segmented phase plate—very easily be converted into a vortex beam, which leads directly to at least a doubling of the laser focus diameter. With the now widened focus the material decomposition may be performed in the predetermined scanning points of a line cut or surface cut which is located substantially perpendicular to the direction of incidence, that is, substantially along the direction of the achieved focus widening. After the execution of the laser cut, the vortex beam can—by slewing out the phase plate—be converted back to the normal beam.

Alternatively, it is possible to deflect the treatment laser beam via at least one controllable deflecting mirror, wherein the one deflection mirror, as a function of its controller, guides the beam path of the laser light through the means for mode conversion or bypassing it.

The inventive means of mode conversion deployable in and out of the in the beam path facilitate the carrying out of cutting essentially perpendicular to the beam incidence direction for each laser wavelength due to the fact that, as a consequence of magnification of the focus diameter, fewer grid points are required in both the disintegration mode and the splitting mode for execution of a cut, which fundamentally increases the cutting speed.

The invention is very advantageous for UV lasers, and particularly when used for cutting into living tissue. Most preferably laser machining can be performed with the invention on a living eye with wavelengths between 300 nm and 400 nm, wherein at the same time the radiation dose is optimized, or at least can be kept lower than a predetermined threshold value.

A further advantageous application of the invention is to suppress a possible focus elongation by nonlinear propagation of the beam in LASIK flap production and lens break-up with ultra-short IR laser pulses. For lens fragmentation or break-up, comparatively weakly focused high-energy laser pulses are used, so there is here a particularly high tendency to filamentation. The at least four-fold increase in the self-focusing threshold with the use of vortex beams leads to a better localization of the energy deposition in the axial direction and therefore to protection the lens capsule and prevention of local maxima of the radiation dose on the retina.

It is also an advantageous embodiment of the inventive laser cutting device, if this has a device for determining the radiation dose per unit area, which detects the irradiation parameters of the laser light source and the predetermined spot positions, calculates therefrom a dose value, and outputs this. In a further preferred embodiment of the laser cutting device, the device for determining the radiation dose per unit area is adapted, upon reaching a dose level which exceeds a predetermined threshold value, to automatically change the irradiation parameters of the laser light source and/or predetermine the spot positions with a greater distance between spots. Such means may be a programmable microprocessor, preferably a PC, which is provided with interfaces for data exchange with the control unit of the scanner, and as required, with the laser light source. It is common that a single computer system monitors and controls the functionality of all components of the laser cutting system. In such a computer system, the arrangement for determining the radiation dose can be realized in the form of a software implementation.

It should be emphasized at this point that, while the invention has a wider range of applications, its use is particularly advantageous in laser in situ keratomileusis (LASIK), flapless refraction correction by cutting out a lenticule, lamellar keratoplasty and/or laser cataract surgery. Moreover, it can also be viewed as a key concept for the introduction of UV laser systems in refractive eye surgery because it offers a solution to the dosing problem.

BRIEF DESCRIPTION OF THE SEVERAL
VIEWS OF THE DRAWINGS

In the following the invention will be explained in greater detail also with reference to the accompanying drawings.

Figure 4:
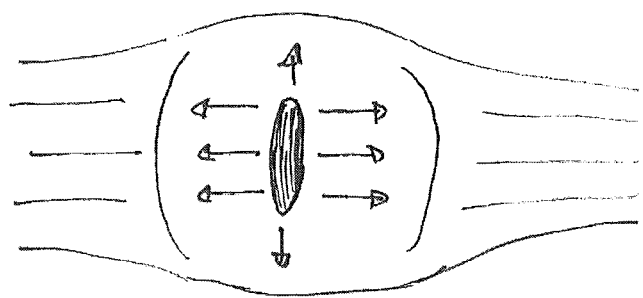
Figure 4:
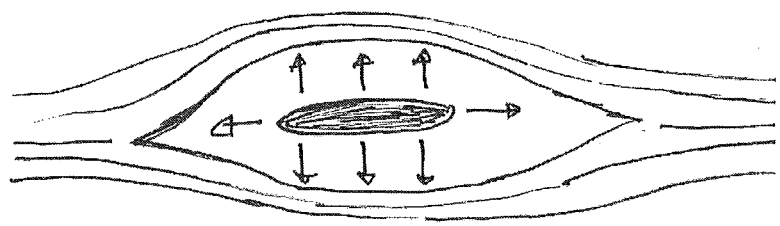

There is shown in:

FIG. 1 a comparison of the shapes of the focus of (a) linear (above) and (b) azimuthal (below) polarized laser radiation;

FIG. 2 a sketch of a segmented phase plate, which may be incorporated as a possible means for mode conversion in the beam path of the laser;

FIG. 3 readings for laser energy in the successful cutting guidance with a UV-laser system in enucleated pig eyes with respect to the spot distance used, in particular, the single-pulse energy (above) (a) and the total dose (below) (b);

FIG. 4 a sketch of the splitting of a lamellar layered material by means of laser deposition in a) a rod-shaped, and b) a disc-shaped laser focus;

FIG. 5 a schematic representation of the apparatus of the invention comprising: a) slewable means for mode conversion and b) controllable deflection mirrors for selecting a light path.

DETAILED DESCRIPTION OF THE INVENTION

As explained above, the introduction of means for mode conversion to a linearly polarized laser beam with, for example Gaussian beam profile, creates a vortex beam (here: with azimuthal polarization). If this is focused into a transparent material, then a toroidal focal volume results as shown in FIG. 1 bottom. The direction of irradiation, is here along the z-axis. For comparison, the focus of the laser without the optical element placed in the beam shown in FIG. 1 top (all figures taken from Hao et al (2010)). The two right-side images show the xz-plane and thus the focal length along the z-direction, which in the Gaussian beam and vortex only slightly differ. From the two left images, however, it is plain to see that in the xy-plane perpendicular to the beam direction the focal diameter of the vortex beam is more than doubled. The singularity at the center of the vortex beam is usually of no relevance for the cutting action. The material is there also either decomposed or at least split, such that the material is destroyed in a disc or disc-shaped volume. Accordingly, one can speak of a disc-shaped laser focus.

A disc-shaped focus can be easily produced by introducing an optical element. For example, a segmented phase plate, preferably made of birefringent quartz glass having a different orientation of the crystal optical axis in each of the individual segments, is used (FIG. 2). The orientation of the slow light beam light propagation direction in the crystal is shown in each case by the direction of the arrow in FIG. 2.

It should be noted that the individual segments are glued together, and the adhesive may degrade when exposed to UV light. Segmented phase plates for short-pulsed UV laser radiation of very high power are therefore still in development. First tests for UV resistance in the laboratory of the present inventors have however been finalized with promising results:

A threshold for visible damage in the adhesive layer by UV degradation was determined to be about $3 \times 10^6$ (3 million) $J/cm^2$. If one assumes that for a planned application a homogeneous illumination of a surface of the mode converter of 10 mm diameter is done with single pulses of about 10 µJ, then to reach this threshold about $2.4 \times 10^{11}$ pulses would have to be applied, which at a repetition rate of 150 kHz would correspond to a lifetime of nearly 440 h.

In a clinical device for LASIK flap production it can be ensured by a shutter in the laser output, that the duty time of the phase plate is the same as the irradiation time of the eye. Since the average cutting time per eye is less than 30 s, it would be possible to treat within the expected lifetime of the phase plate 52800 eyes. Assuming a treatment duration per patient of about 15 minutes for both eyes, the phase plate needs to be replaced after about 5 years.

It has not yet been proposed, to the knowledge of the inventors, to equip a laser cutting device for transparent material with a focus deliberately widened by helical laser light. At first glance, it is also not obvious to the person of ordinary skill in the art, because of the generally desired lateral cutting accuracy is deteriorated. When cutting along lines or surfaces that are oriented substantially perpendicular to the direction of incidence, then it is not so much the lateral, but mainly the axial cutting precision that is important. The latter is even improved by the invention, because by reducing the splitting distance to be overcome the cutting guidance remains better confined in the range of the cutting plane.

The following considerations serve to illustrate the advantages that can be achieved with respect to the total irradiation dose and the cutting precision by the helical laser light and the therewith generated disc-shaped laser foci:

When cutting in the disintegration mode, the spot interval D is smaller than the focus diameter d, while in comparison it is greater in the splitting mode. In the transition between cutting in the disintegration mode and cutting in the splitting mode, the radius of the cut surface produced during application of a laser pulse corresponds precisely to the half of the focal diameter d/2. For a focal distance D>d in each case the distance $(D/2-d/2)=(D-d)/2$ must be overcome by splitting. The mechanical work required for this is introduced by the energy of the laser-induced shock wave and cavitation bubble. The laser energy $E_{tot}$ required for cutting a surface element depends on D and the single pulse energy $E_L$. With pulse energy $E_L$ being constant, the following would apply $$E_{tot} \propto \frac{1}{D^2}, \tag{3}$$

because the number of laser pulses per area element decreases quadratically with D. Actually, the pulse energy is, however, not a constant, but must be chosen such that it creates a bubble of a size sufficient to reliably span the distance between adjacent grid points by splitting. The possible range of the splitting can be estimated by the maximum radius $R_{max}$ of the bubbles, wherein for a reliable cleavage this should always be greater by a particular factor k>1 than half the grid point spacing:

$$R_{max} = k \times D/2 \tag{4}$$

The prior art recognizes the following relationship between the laser pulse energy $E_L$ and the maximum radius of the cavitation bubbles generated in water:

$$R_{max} \propto (E_L - E_c)^{1/3}, \tag{5a}$$

wherein $E_c$ is the amount of energy which is transmitted through the focus during the laser pulse before the plasma formation threshold is reached. Near the threshold (5a) rapidly increases pursuant to Rmax at first with $E_L$, but for pulse energies well above the plasma formation threshold the increase slows down, since $E_L >> E_c$ applies and thus approximately.

$$R_{max} \propto E_L^{1/3}. \tag{5b}$$

Although the details of the cutting dynamics in the corneal tissue are still poorly understood, the weak dependence between $R_{max}$ and $E_L$ in equation (5b) already suggest that in the case of a large grid point distance D>>d a significant increase in single-pulse energy will be required to overcome a growing distance (D-d)/2 by splitting. In the extreme cases, when the focus diameter d compared to the spot interval D is negligibly small, ultimately with equations (4) and (5b) the following applies:

$$E_L \propto D^3 \quad (6)$$

An increase of D leads, in the case of small values of the grid point spacing, due to the reduced number of pulses per area element, initially to a significant reduction in the total energy required for cutting, i.e., in equation (3) the dependence $E_{tot}$ (D) dominates. For larger grid point intervals, the increase in the required single-pulse energy largely compensates for the effect of reduced pulse count or rate. For even larger grid point spacing it is expected that the increase in the required single-pulse energy according to equation (6) finally the effect of the reduced number of pulses dominates according to equation (3), and the required total cutting energy even increases with D.

Experiments on enucleated porcine eyes illustrate the aforementioned situation. FIG. 3 shows, following several successfully executed laser dissections at different numerical apertures (NA), the required single pulse energies (top) and the total irradiation doses (bottom), respectively, depending on the spot distance. While the pulse energy needed to be approximately tripled during the transition from 3 microns to 12 microns spot distance, at the same time the total radiation dose decreased by approximately one-sixth. It could also already be seen that the total dose can not be decreased any further by a further enlargement of the spot spacing while simultaneously increasing the pulse energy. However it would then be expected to increase possible side effects in the area of the spots.

The expansion of the focus diameter d at constant grid spacing D possible through the inventive device now reduces the splitting distance (D–d)/2 to be overcome, and thus reduces the required mechanical cutting work that needs to be applied by the shock wave and cavitation bubble. If the focus diameter is increased, for example from 1 µm to 3 µm, then the area cut by disintegration in the plasma increases nine-fold. With a 6 µm grid point spacing, this corresponds to a significant increase of the proportion of the area cut by disintegration. It increases from only about 1/46 to just under 1/5.

A disc-shaped focus supports, in particular in a lamellar stratified structure such as the cornea, a cleaving along the direction of the strata, since by the force distribution in the plasma- and bubble-expansion, the strata are moved apart and a preferred direction and preferred plane for splitting are defined by the alignment of the focus disc. The sketch in FIG. 4 represents the splitting of corneal lamellae by energy deposition a) in a rod-like laser focus and b) in a disc-shaped focus. The arrows indicate the directions of the outward radiating power of the foci effects. It is easy to see that the disc-shaped focus better supports the detachment of the lamella from each other than the rod-like focus. The lateral cleaving of the material by application of helical laser pulses has therefore for each individual spot a longer range and thus makes possible cutting with less grid points. In addition, the axial cutting precision is improved, since by reducing the cleaving distance to be overcome the cut direction remains better localized in the incision plane.

Finally, two embodiments of the inventive laser cutting device are sketched in FIG. 5.

In FIGS. 5 a) and b) respectively show one laser 1 is shown, which emits a pulsed laser beam 2. The wavelength of the laser beam 2 can be ultraviolet or infrared, or originate from the visible spectrum, and is preferably between about 300 and 1100 nm. In a particularly preferred embodiment of the invention, the laser 1 is a UV laser with a wavelength between 300 and 400 nm.

In the prior art, the pulsed laser beam 2 is directed to a deflection unit 20 (scanner) which deflects the laser beam 2 to a predetermined direction. The deflected laser beam is expanded by an expanding telescope 21 and focused by a cutting lens 22 into a sample of transparent material 23. The laser focus lies on a predetermined point on a predetermined cutting line or area 24. A control unit 30 can control the laser source 1 and the deflection unit 20 in order to change irradiation parameters and/or in particular to predetermine a different location of the laser focal point (spot) on the cutting line or area 24. The control unit 30 normally operates programmatically, i.e. it generally comprises a programmable computing unit such as a PC.

Novel, compared to the prior art, is the means of mode conversion 3 that can be introduced into and removed from the beam path of the pulsed laser beam 2, in which the transitioning pulsed laser beam 2 is converted into a pulsed laser beam having a helical phase front 5. Suitable means of mode conversion are helical phase plates, wherein for high-performance applications currently segmented helical phase plates are available, which are composed of birefringent segments with differently oriented optical axes (see FIG. 2).

It is not absolutely necessary to the invention, but very beneficial in the case of use of segmented phase plates, to position a spatial filter (or: spatial frequency filter) 4 in the beam path behind the phase plate. Above all, undesirable laser light scattered at the segment boundaries is removed from the pulsed helical laser beam 5. The spatial filtering for "beam cleaning" is known to those skilled in the laser art itself.

According to FIG. 5 a) the means of mode conversion 3 and the spatial filter 4 are collectively slewed into the beam path, indicated by the vertical double arrow. The slewing operation here includes any type of mechanical movement of the means for mode conversion 3 and the spatial filter 4, with at least one end position being in a co-axial alignment with the laser beam direction. If the means of mode conversion 3 and the spatial filter 4 are brought into said end position (swung into the beam path), then the conversion of the pulsed laser beam 2 in a pulsed laser beam having a helical phase front 5 occurs. Following retraction of the components 3 and 4, the laser beam 2 instead of 5 is again available.

Mechanical means for advancing and retracting the means for mode conversion 3 and spatial filter 4 are technically simple and inexpensive, but not necessarily in all cases suitable for the rapid change from normal laser beam 2 to helical laser beam 5 or vice versa in short time intervals.

Accordingly, as an alternatively, it is shown in FIG. 5 b), that instead of the now fixed means for mode conversion 3 and fixed spatial filter 4, it is the beam path of the laser light 2 that is deflected by mirrors 6, 7, 8, 9. Therein the mirrors 7 and 8 are fixed, and the mirrors 6 and 9 are pivotable or can be folded out. By virtue of a—not shown—controller the user can decide, by choosing the mirror position of the mirrors 6 and 9, whether the pulsed laser beam 2 is to pass through the means for mode conversion 3 and the spatial filter 4 and is to be converted into the pulsed helical laser beam 5, or whether it is to bypass the means for mode conversion at 3 and spatial filter 4.

Finally, it should be noted that the above-mentioned device for determining the radiation dose is preferably integrated as a software module (such as selectable subroutine) in the programming of the control unit 30. The device then has available the irradiation parameters and the selectable spot grid already before performing the irradiation. It can, on the basis of this precalculation, provide a dose value of the radiation dose or can activate a warning display when the calculated dose value exceeds a predetermined threshold.

In a preferred embodiment of the invention the software module ensures that, for pre-selected laser parameters with very close-knit spot grid, which would lead to exceeding the predetermined threshold radiation dose per unit area, these can no longer be selected or can only be activated following special release by the user.

LIST OF REFERENCE NUMERALS

1 Laser
2 Pulsed laser beam
3 Means of mode conversion
4 Spatial filter for "beam cleaning"
5 Pulsed laser beam having a helical phase front
6, 9 Pivotable mirror
7, 8 Mirrors
20 Deflector
21 Expanding telescope
22 Cutting lens
23 Specimen of transparent material, e.g. cornea
24 Incision line or area
30 Control unit

The invention claimed is:

1. A laser cutting device for cutting a transparent tissue of an eye, the device adapted to focus laser light into a plurality of predetermined spots in the transparent tissue, wherein the spots are located on a predetermined cutting line or cutting area in a direction substantially perpendicular to the direction of incidence of the laser light, the device comprising:
   a laser for generating a laser beam,
   a means for mode conversion of the laser beam into laser light having a helical phase front,
   a means for focusing the laser light to a focus,
   a means for steering the focus along the plurality of predetermined spots on a predetermined cutting line or cutting area, and
   a means for placing the means for mode conversion either into or out of the beam path of the laser light, comprising
      at least one controllable deflection mirror located between the laser and the means for mode conversion, or
      a mechanical movement means, connected to at least the means for mode conversion, for moving the means for mode conversion into or out of the beam path.

2. A laser cutting device for cutting a transparent tissue of an eye, the device adapted to focus laser light into a plurality of predetermined spots in the transparent tissue, wherein the spots are located on a predetermined cutting line or cutting area in a direction substantially perpendicular to the direction of incidence of the laser light, the device comprising:
   a laser for generating a laser beam,
   a means for mode conversion of the laser beam into laser light having a helical phase front,
   a means for focusing the laser light to a focus, and
   a means for steering the focus along the plurality of predetermined spots on a predetermined cutting line or cutting area,
   a means for placing the means for mode conversion either into or out of the beam path of the laser light, comprising
      at least one controllable deflection mirror located between the laser and the means for mode conversion or
      a mechanical movement means, connected to at least the means for mode conversion, for moving the means for mode conversion into or out of the beam path,
   wherein
   the means of mode conversion include a helical phase plate.

3. The laser cutting device according to claim 2, wherein
   the helical phase plate is composed of birefringent segments with respective differently oriented optical axes.

4. The laser cutting device according to claim 1, wherein said means for placing the means for mode conversion either into or out of the beam path of the laser light comprises at least one controllable deflection mirror between the laser and the means for mode conversion which, in response to its controller, directs the beam path of the laser light either (a) through the means for mode conversion or (b) past it.

5. A laser cutting device for cutting a transparent tissue of an eye, the device adapted to focus laser light into a plurality of predetermined spots in the transparent tissue, wherein the spots are located on a predetermined cutting line or cutting area in a direction substantially perpendicular to the direction of incidence of the laser light, the device comprising:
   a laser for generating a laser beam,
   a means for mode conversion of the laser beam into laser light having a helical phase front,
   a means for focusing the laser light to a focus,
   a means for steering the focus along the plurality of predetermined spots on a predetermined cutting line or cutting area, and
   a means for placing the means for mode conversion either into or out of the beam path of the laser light comprising
      at least one controllable deflection mirror located between the laser and the means for mode conversion or
      a mechanical movement means connected to at least the means for mode conversion for moving the means for mode conversion into or out of the beam path,
   wherein
   a spatial frequency filter is arranged in the beam path of the laser light, downstream of the means for mode conversion.

6. The laser cutting device according to claim 1, wherein
   the laser light source emits pulsed ultraviolet light at a wavelength between 300 nm and 400 nm.

7. The laser cutting device according to claim 1, wherein
   a device for determining the radiation dose per unit area is provided, which detects the irradiation parameters of the laser light source and the spot positions predetermined by the control device of the deflector, and from this calculates a dose value, and outputs this, or activates a warning display upon exceeding a predetermined threshold.

8. A method for laser cutting optically transparent tissue of an eye, comprising
   using a laser to generate a laser beam,
   directing the laser beam into the eye generally perpendicular to the surface of the cornea and focusing via a means for focusing the laser light the laser radiation on target points arranged in a pattern generally parallel to the surface of the cornea via a means for steering the focus, introducing into the laser beam a means for mode conversion of the laser beam into laser light having a helical phase front, and radiating each target point for a sufficient time and intensity to cut an area of the transparent tissue using the laser light with the helical phase front.

9. The method according to claim 8 further comprising creating a corneal flap by cutting along at least a part of the periphery of the cut area using a Gaussian laser beam or Bessel laser beam.

10. A laser cutting device for cutting a transparent tissue of an eye, the device adapted to focus laser light into a plurality of predetermined spots in the transparent tissue, wherein the spots are located on a predetermined cutting line or cutting area in a direction substantially perpendicular to the direction of incidence of the laser light, the device comprising:

a laser for generating a Gaussian beam, a means for mode conversion of the Gaussian beam into laser light having a helical phase front, a means for placing the means for mode conversion either into or out of the beam path of the Gaussian beam, comprising at least one controllable deflection mirror located between the laser and the means for mode conversion, or a mechanical movement means, connected to at least the means for mode conversion, for moving the means for mode conversion into or out of the beam path, a means for focusing the laser light to a focus, and a means for steering the focus along the plurality of predetermined spots on a predetermined cutting line or cutting area.

* * * * *